United States Patent
McCaffrey et al.

(10) Patent No.: US 11,852,345 B2
(45) Date of Patent: *Dec. 26, 2023

(54) PRE-DIFFUSER FOR A GAS TURBINE ENGINE

(71) Applicant: RTX Corporation, Farmington, CT (US)

(72) Inventors: Michael G. McCaffrey, Windsor, CT (US); Matthew Andrew Hough, West Simsbury, CT (US); Pedro E. Rivero, Miami, FL (US)

(73) Assignee: RTX Corporation, Farmington, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/846,412

(22) Filed: Jun. 22, 2022

(65) Prior Publication Data

US 2023/0089675 A1 Mar. 23, 2023

Related U.S. Application Data

(63) Continuation of application No. 16/376,448, filed on Apr. 5, 2019, now Pat. No. 11,371,704.

(51) Int. Cl.
*F23R 3/10* (2006.01)
*F04D 29/54* (2006.01)
(Continued)

(52) U.S. Cl.
CPC ............ *F23R 3/10* (2013.01); *C07K 16/2863* (2013.01); *F01D 9/041* (2013.01); *F04D 29/545* (2013.01); *F23R 3/005* (2013.01); *C07K 2317/31* (2013.01); *C07K 2317/622* (2013.01); *C07K 2317/626* (2013.01); *F05D 2230/60* (2013.01); *F05D 2240/12* (2013.01); *F05D 2240/35* (2013.01); *F05D 2240/55* (2013.01)

(58) Field of Classification Search
None
See application file for complete search history.

(56) References Cited

U.S. PATENT DOCUMENTS

| | | |
|---|---|---|
| 4,416,111 A | 11/1983 | Enahan |
| 4,503,668 A | 3/1985 | Duncan, III et al. |

(Continued)

FOREIGN PATENT DOCUMENTS

| | | |
|---|---|---|
| EP | 1223382 A2 | 7/2002 |
| EP | 3034797 A1 | 6/2016 |

(Continued)

OTHER PUBLICATIONS

European Search Report dated Jun. 12, 2020 issued for corresponding European Patent Application No. 20166491.9.

(Continued)

*Primary Examiner* — Todd E Manahan
*Assistant Examiner* — Sean V Meiller
(74) *Attorney, Agent, or Firm* — Bachman & LaPointe, P.C.

(57) ABSTRACT

A hot fairing structure for a pre-diffuser includes a ring-strut-ring structure that comprises a multiple of hollow struts and a multiple of inlets to a respective diffusion passage, one of the multiple of inlets formed between each one of the multiple of hollow struts located between two diffusion passages.

11 Claims, 11 Drawing Sheets

(51) Int. Cl.
*F01D 9/04* (2006.01)
*F23R 3/00* (2006.01)
*C07K 16/28* (2006.01)

(56) References Cited

U.S. PATENT DOCUMENTS

| | | | |
|---|---|---|---|
| 4,793,770 A | 12/1988 | Schonewald et al. | |
| 5,249,921 A * | 10/1993 | Stueber | F04D 29/542 |
| | | | 415/138 |
| 5,632,141 A | 5/1997 | Sloop et al. | |
| 5,868,553 A | 2/1999 | Battig et al. | |
| 6,364,606 B1 * | 4/2002 | Rice | F01D 25/246 |
| | | | 415/214.1 |
| 6,513,330 B1 | 2/2003 | Rice et al. | |
| 7,819,622 B2 | 10/2010 | Paulino | |
| 9,631,517 B2 | 4/2017 | Liles et al. | |
| 9,951,692 B2 | 4/2018 | Aronsson et al. | |
| 10,060,631 B2 | 8/2018 | Lyons | |
| 10,161,414 B2 | 12/2018 | Eastwood | |
| 10,288,289 B2 | 5/2019 | Astwood | |
| 10,344,623 B2 | 7/2019 | Eastwood | |
| 10,533,437 B2 | 1/2020 | Dale | |
| 2004/0041350 A1 | 3/2004 | Beeck et al. | |
| 2004/0093871 A1 | 5/2004 | Burrus et al. | |
| 2009/0148297 A1 | 6/2009 | Suciu et al. | |
| 2014/0186167 A1 | 7/2014 | Liles et al. | |
| 2015/0252729 A1 * | 9/2015 | Niggemeier | F02C 6/08 |
| | | | 415/213.1 |
| 2016/0169049 A1 * | 6/2016 | Eastwood | F01D 25/24 |
| | | | 415/213.1 |
| 2016/0169245 A1 | 6/2016 | Astwood et al. | |
| 2016/0201688 A1 * | 7/2016 | Lyons | F01D 5/081 |
| | | | 60/751 |
| 2017/0343011 A1 | 11/2017 | Schwarz | |
| 2020/0318652 A1 | 10/2020 | McCaffrey et al. | |
| 2020/0318833 A1 | 10/2020 | McCaffrey et al. | |

FOREIGN PATENT DOCUMENTS

| | | |
|---|---|---|
| EP | 3034804 A1 | 6/2016 |
| FR | 2887924 A1 | 1/2007 |
| WO | 2014052737 A1 | 4/2014 |
| WO | 2015017000 A2 | 2/2015 |
| WO | 2015031796 A1 | 3/2015 |

OTHER PUBLICATIONS

European Search Report dated Jun. 12, 2020 issued for corresponding European Patent Application No. 20166838.1.
European Search Report dated Jun. 12, 2020 issued for corresponding European Patent Application No. 20166506.4.
U.S. Non-Final Office Action dated Sep. 2, 2020 issued for corresponding U.S. Appl. No. 16/376,451.
U.S. Non-Final Office Action dated Oct. 15, 2020 issued for corresponding U.S. Appl. No. 16/376,445.
U.S. Non-Final Office Action dated Feb. 23, 2021 issued for corresponding U.S. Appl. No. 16/376,445.

* cited by examiner

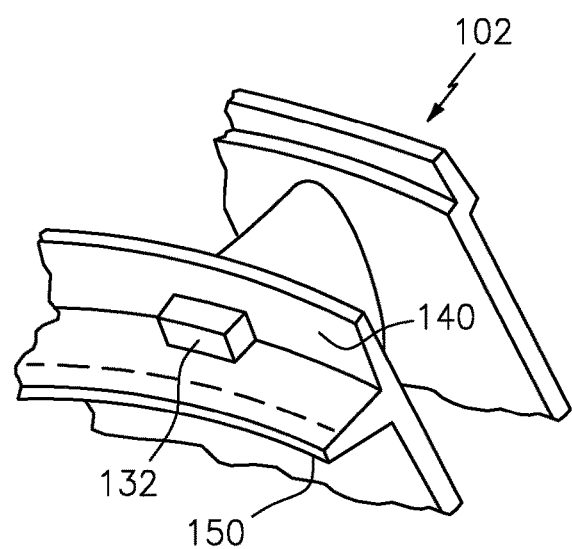
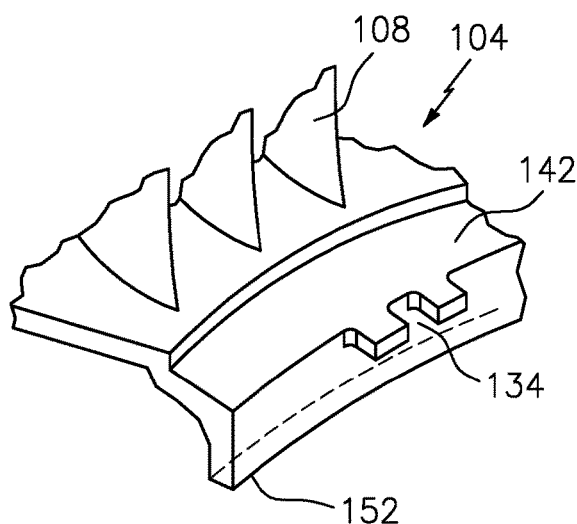
FIG. 7          FIG. 8
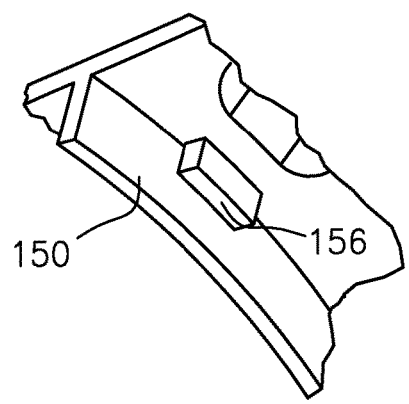
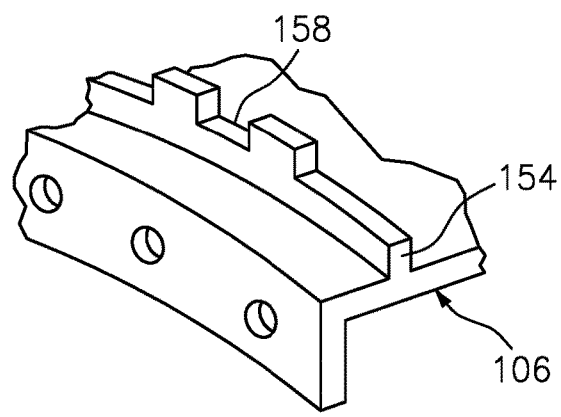
FIG. 9          FIG. 10

PRE-DIFFUSER FOR A GAS TURBINE ENGINE

CROSS-REFERENCE TO RELATED APPLICATIONS

This application is a continuation of U.S. patent application Ser. No. 16/376,448 filed Apr. 5, 2019.

BACKGROUND

The present disclosure relates to a gas turbine engine and, more particularly, to a pre-diffuser therefor.

Gas turbine engines include a compressor section to pressurize a supply of air, a combustor section to burn a hydrocarbon fuel in the presence of the pressurized air, and a turbine section to extract energy from the resultant combustion gases. The compressor section discharges air into a pre-diffuser upstream of the combustion section. The pre-diffuser converts a portion of dynamic pressure to static pressure. A diffuser receives the air from the pre-diffuser and supplies the compressed core flow around an aerodynamically-shaped cowl of the combustion chamber. The core flow is typically separating into three branches. One branch is the cowl passage to supply air to fuel nozzles and for dome cooling. The other branches are annular outer plenum and inner plenums where air is introduced into the combustor for cooling and to complete the combustion process. A further portion of the air may be utilized for turbine cooling.

The pre-diffuser is exposed to large thermal gradients and requires various features for anti-rotation, axial retention, and centrality with respect to the central engine axis. These features may result in local discontinuities which may generate stress risers and consequently reduced operational life.

SUMMARY

A hot fairing structure for a pre-diffuser according to one disclosed non-limiting embodiment of the present disclosure includes a ring-strut-ring structure that comprises a multiple of hollow struts and a multiple of inlets to a respective diffusion passage, one of the multiple of inlets formed between each one of the multiple of hollow struts located between two diffusion passages.

A further aspect of the present disclosure includes that the hot fairing structure is a full ring structure.

A further aspect of the present disclosure includes that each of the multiple of hollow struts include a cavity.

A further aspect of the present disclosure includes a passage in communication with the cavity.

A further aspect of the present disclosure includes that the passage is in communication with a combustor section of the gas turbine engine.

A further aspect of the present disclosure includes that the inlet to each of the multiple of diffusion passages are smaller than an exit from the diffusion passage.

A further aspect of the present disclosure includes that the inlet to each of the multiple of diffusion passages are smaller than an exit from the diffusion passage.

A further aspect of the present disclosure includes that each of the multiple of hollow struts align with one of a respective multiple of exit guide vanes of an exit guide vane ring.

A further aspect of the present disclosure includes that the ring-strut-ring structure is cast.

A further aspect of the present disclosure includes a full ring hot fairing radial flange that extends transverse to the multiple of diffusion passages.

A further aspect of the present disclosure includes a first anti-rotation feature on one side of the full ring hot fairing radial flange and a second anti-rotation feature on an opposite side of the full ring hot fairing radial flange.

A further aspect of the present disclosure includes that the first anti-rotation feature engages an exit guide vane ring.

A further aspect of the present disclosure includes that the second anti-rotation feature engages a static structure.

A further aspect of the present disclosure includes that the static structure is subjected to a lower temperature than the ring-strut-ring structure.

A pre-diffuser for a gas turbine engine according to one disclosed non-limiting embodiment of the present disclosure includes an exit guide vane ring having a multiple of exit guide vanes defined around an engine longitudinal axis; and a hot fairing structure adjacent to the exit guide vane ring to form a multiple of diffusion passages defined around the engine longitudinal axis, the hot fairing structure comprises a ring-strut-ring structure with a multiple of hollow struts and a multiple of inlets to the respective multiple of diffusion passages, one of the multiple of inlets formed between each of the multiple of hollow struts.

A further aspect of the present disclosure includes that each of the multiple of hollow struts includes a cavity.

A further aspect of the present disclosure includes a passage in communication with each cavity.

A further aspect of the present disclosure includes an outer radial interface between a radial outer surface of the hot fairing structure and the exit guide vane ring, the outer radial interface being a full hoop structure; and an anti-rotation feature between the hot fairing structure and the exit guide vane ring, the anti-rotation features inboard of the multiple of diffusion passages.

A further aspect of the present disclosure includes a hot fairing radial flange that extends radially inward from the hot fairing structure and an exit guide vane radial flange that extends radially inward from the exit guide vane ring, the seal located between the exit guide vane radial flange and the hot fairing radial flange.

A further aspect of the present disclosure includes a static structure flange that abuts the hot fairing radial flange; a clamp ring that abuts the exit guide vane radial flange; and a multiple of fasteners that fasten the clamp ring to the static structure flange.

The foregoing features and elements may be combined in various combinations without exclusivity, unless expressly indicated otherwise. These features and elements as well as the operation of the invention will become more apparent in light of the following description and the accompanying drawings. It should be understood, however, the following description and drawings are intended to be exemplary in nature and non-limiting.

BRIEF DESCRIPTION OF THE DRAWINGS

Various features will become apparent to those skilled in the art from the following detailed description of the disclosed non-limiting embodiment. The drawings that accompany the detailed description can be briefly described as follows:

FIG. 7 is a perspective view of the hot fairing structure of the pre-diffuser.

FIG. 8 is a perspective view of the exit guide vane ring of the pre-diffuser.

FIG. 9 is a perspective view of the hot fairing structure from an opposite direction as that of FIG. 7.

FIG. 10 is a perspective view of the static structure.

DETAILED DESCRIPTION

Figure 1:
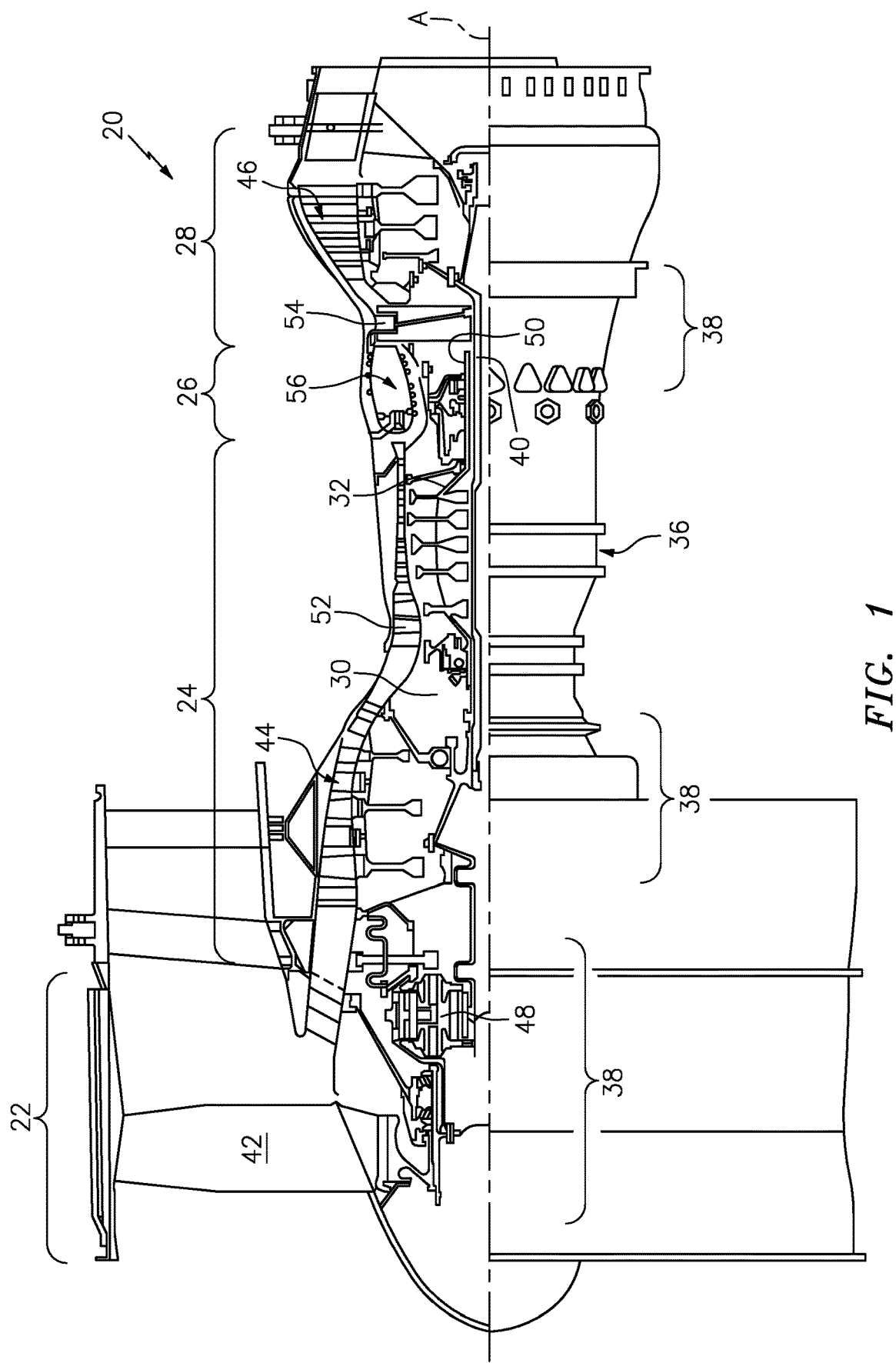
FIG. 1 is a schematic cross-section of a gas turbine engine.

FIG. 1 schematically illustrates a gas turbine engine 20. The gas turbine engine 20 is disclosed herein as a two-spool turbofan that generally incorporates a fan section 22, a compressor section 24, a combustor section 26 and a turbine section 28. Alternative engines might include other systems or features. The fan section 22 drives air along a bypass flowpath while the compressor section 24 drives air along a core flowpath for compression and communication into the combustor section 26, then expansion through the turbine section 28. Although depicted as a turbofan gas turbine engine in the disclosed non-limiting embodiment, it should be understood that the concepts described herein are not limited to use with turbofans as the teachings may be applied to other types of turbine engines.

The engine 20 generally includes a low spool 30 and a high spool 32 mounted for rotation about an engine central longitudinal axis A relative to an engine case structure 36 via several bearing structures 38. The low spool 30 generally includes an inner shaft 40 that interconnects a fan 42, a low pressure compressor (LPC) 44 and a low pressure turbine (LPT) 46. The inner shaft 40 drives the fan 42 directly or through a geared architecture 48 to drive the fan 42 at a lower speed than the low spool 30. An exemplary reduction transmission is an epicyclic transmission, namely a planetary or star gear system.

The high spool 32 includes an outer shaft 50 that interconnects a high pressure compressor (HPC) 52 and high pressure turbine (HPT) 54. A combustor 56 is arranged between the HPC 52 and the HPT 54. The inner shaft 40 and the outer shaft 50 are concentric and rotate about the engine central longitudinal axis A which is collinear with their longitudinal axes. Core airflow is compressed by the low pressure compressor 44, then the high pressure compressor 52, mixed with the fuel and burned in the combustor 56, then expanded over the HPT 54 and LPT 46. The HPT 54 and LPT 46 rotationally drive the respective high spool 32 and low spool 30 in response to the expansion.

Figure 2:
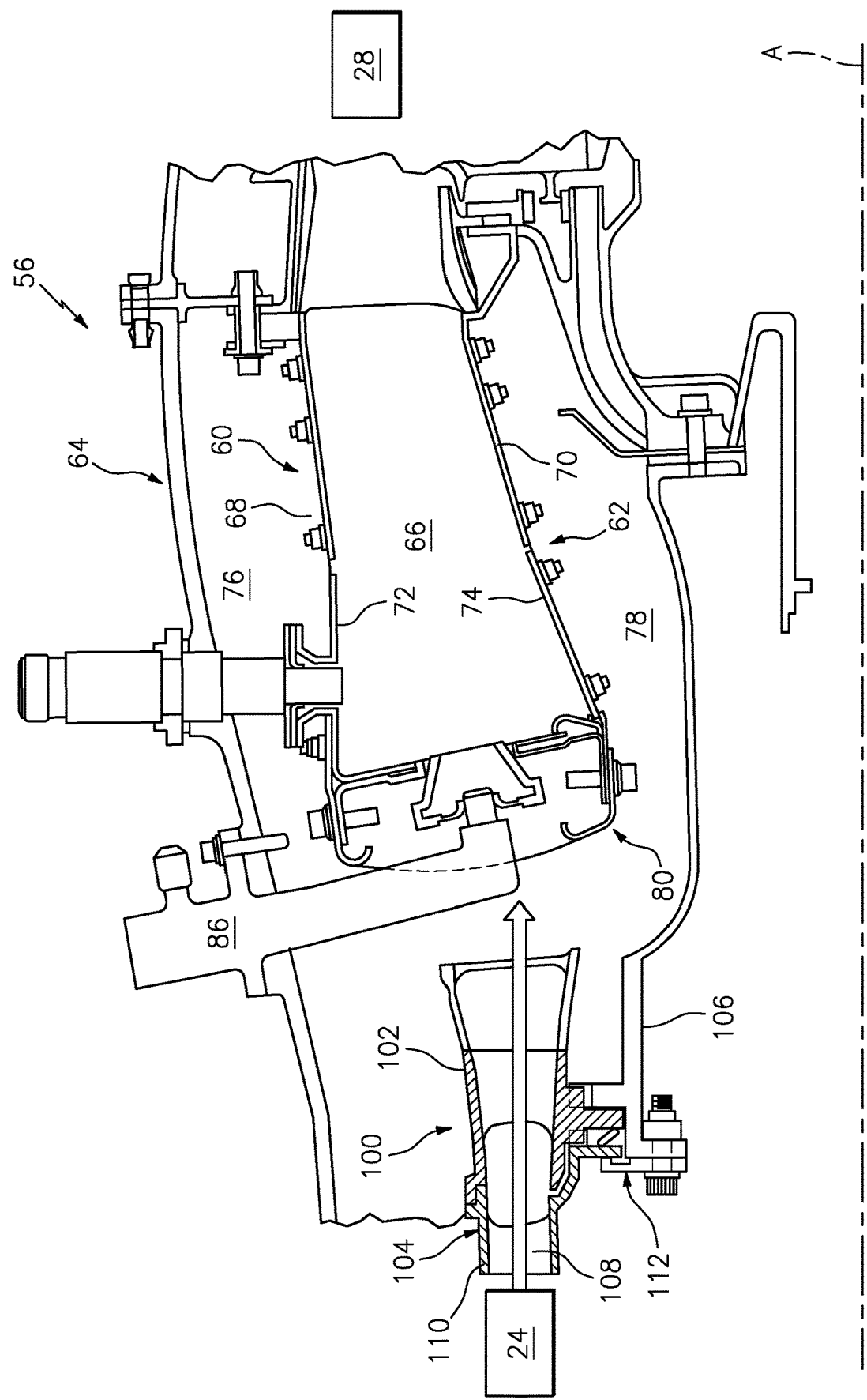
FIG. 2 is a partial longitudinal cross-sectional view of a pre-diffuser according to one non-limiting embodiment that may be used with the gas turbine engine shown in FIG. 1.

With reference to FIG. 2, the combustor 56 generally includes an outer liner 60, an inner liner 62 and a diffuser case module 64. The outer liner 60 and the inner liner 62 are spaced apart such that a combustion chamber 66 is defined therebetween. The combustion chamber 66 is generally annular in shape. The outer liner 60 and the inner liner 62 are spaced radially inward of the outer diffuser case 64 to define an annular outer plenum 76 and an annular inner plenum 78. It should be understood that although a particular combustor is illustrated, other combustor types with various combustor liner arrangements will also benefit herefrom. It should be further understood that the disclosed cooling flow paths are but an illustrated embodiment and should not be limited only thereto.

The liners 60, 62 contain the combustion products for direction toward the turbine section 28. Each liner 60, 62 generally includes a respective support shell 68, 70 which supports one or more heat shields 72, 74 that are attached thereto with fasteners 75.

The combustor 56 also includes a forward assembly 80 downstream of the compressor section 24 to receive compressed airflow through a pre-diffuser 100 into the combustor section 26. The pre-diffuser 100 includes a hot fairing structure 102 and an exit guide vane ring 104. The exit guide vane ring 104 includes a row of Exit Guide Vanes (EGVs) 108 downstream of the HPC 52. The EGVs 108 are static engine components which direct core airflow from the HPC 52 between outboard and inboard walls 110 and 112.

The pre-diffuser 100 is secured to a static structure 106 to at least partially form the diffuser module between the compressor section 24 and the combustor section 26. The hot fairing structure 102 is exposed to large thermal gradients and directs the core airflow while forming a shell within the relatively colder static structure 106. The static structure 106 is thereby segregated from the core airflow and generally operates at a relatively lower temperature than the hot fairing structure 102. The hot fairing structure 102 and the exit guide vane ring 104 are full ring structures that are assembled in a manner that allows common thermal growth yet still remain centered with respect to the static structure 106 along the engine central longitudinal axis A.

Figure 3:
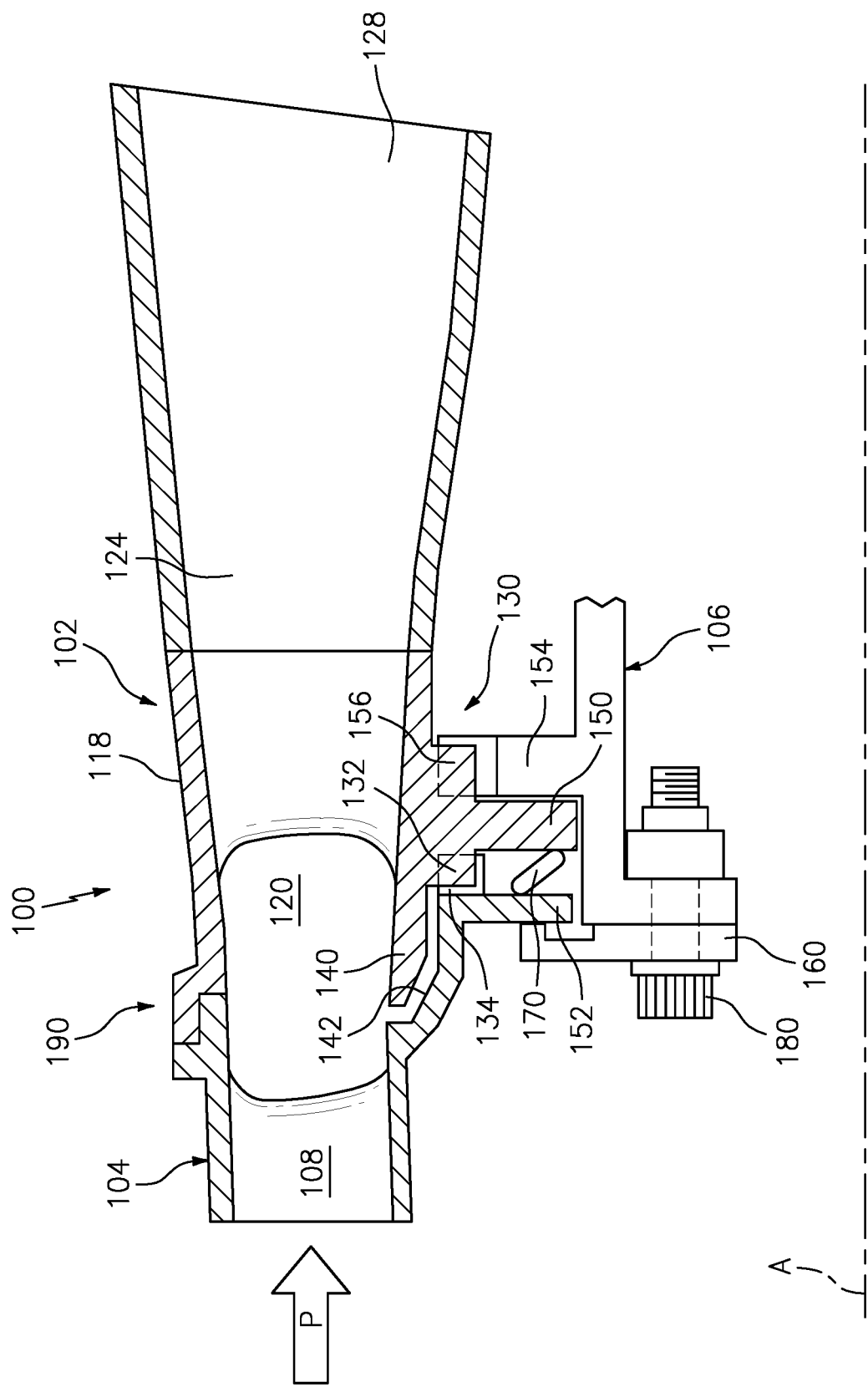
FIG. 3 is an expanded cross-sectional view of the pre-diffuser.
Figure 4:
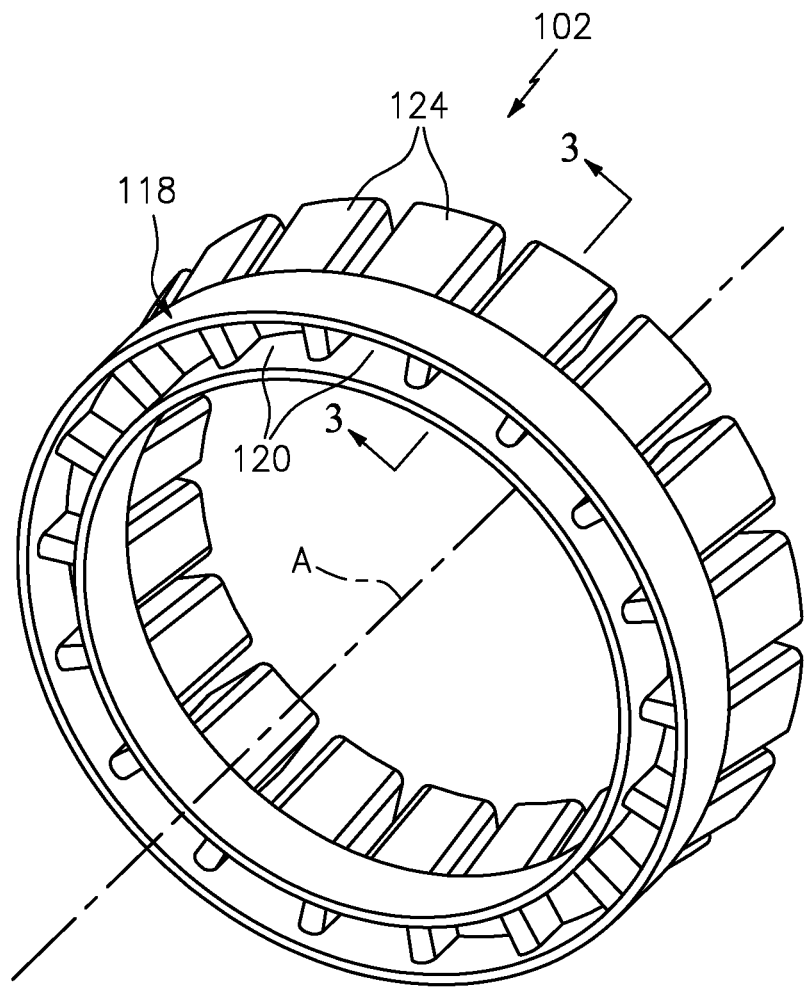
FIG. 4 is a perspective view of the pre-diffuser.
Figure 5:
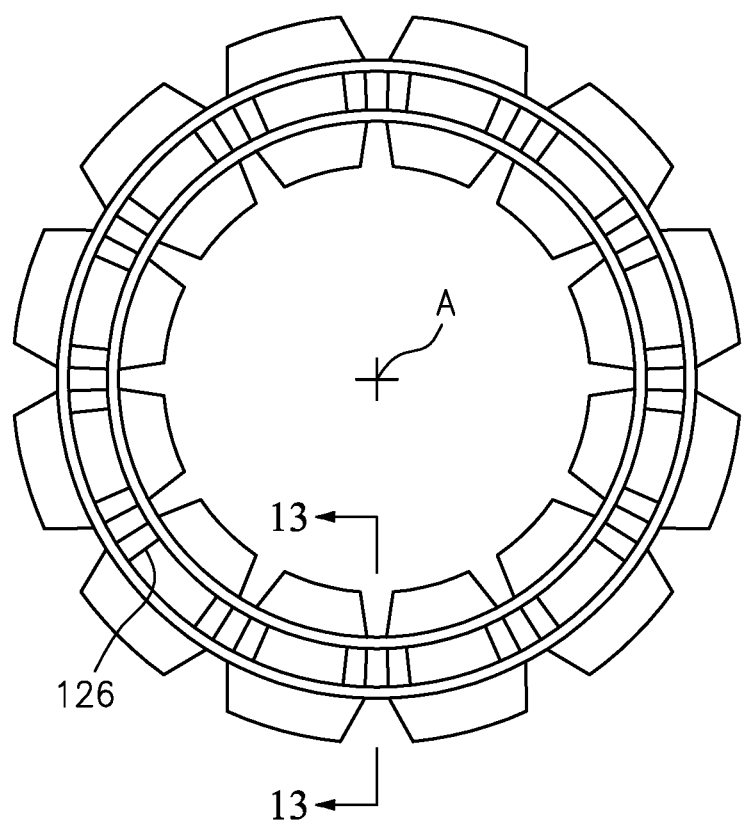
FIG. 5 is a view from front of the pre-diffuser.
Figure 6:
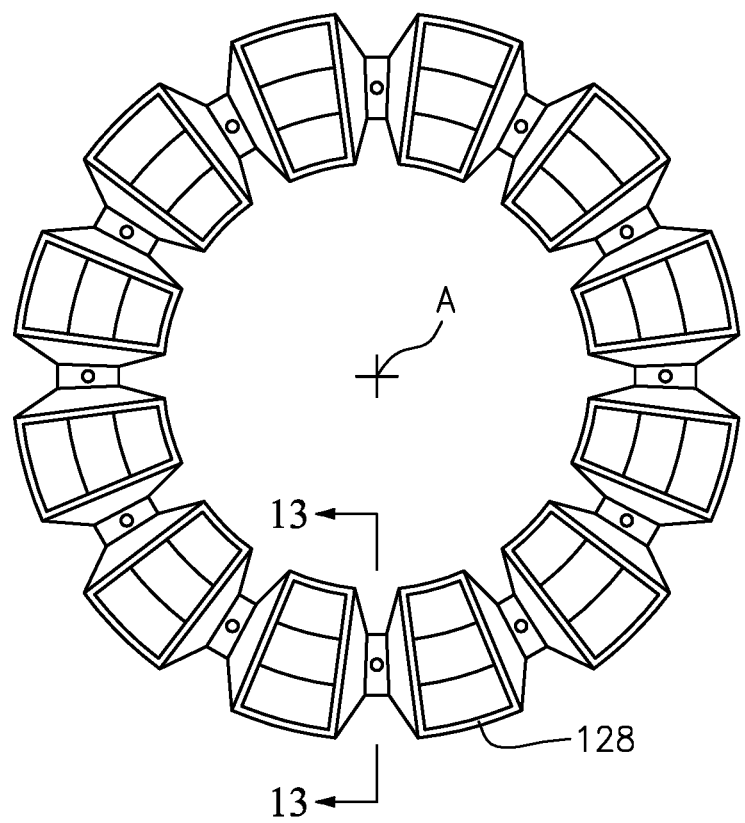
FIG. 6 is a view from rear of the pre-diffuser.
Figure 11:
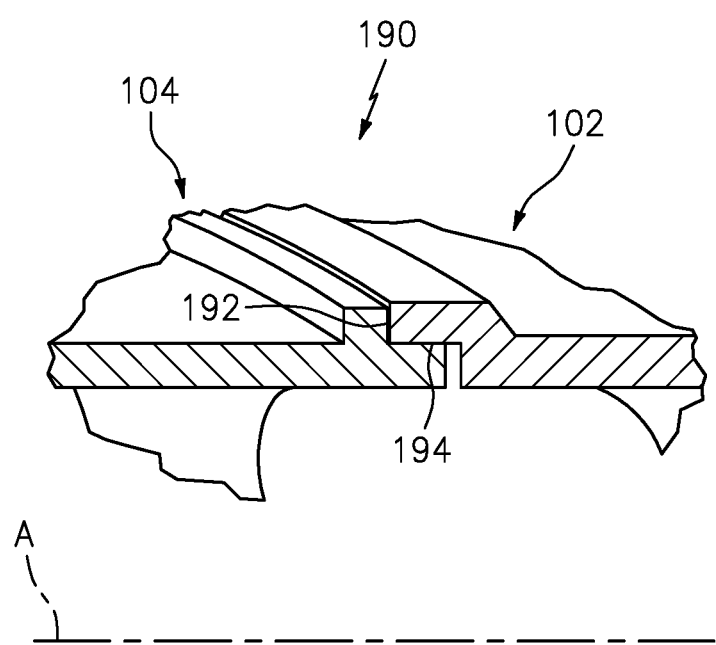
FIG. 11 is an expanded longitudinal cross-sectional view of an outer radial interface between the hot fairing structure 102 and the exit guide vane ring of the pre-diffuser.

With reference to FIG. 3, the hot fairing structure 102 includes a ring-strut-ring structure 118 which forms a multiple of diffusion passages 120 that each communicate with one of a multiple of diffusion passage ducts 124 (FIG. 4) that extend the diffusion passage of the ring-strut-ring structure 118 along each flow passage P. Each of the diffusion passages 120 in the ring-strut-ring structure 118 includes an inlet to the pre-diffuser 100 and a diffusion passage exit that mates with the diffusion passage duct 124. Each of the diffusion passage ducts 124 include a diffusion duct inlet 126 (FIG. 5) adjacent to the ring-strut-ring structure 118. A diffusion duct exit 128 from each diffusion passage duct 124 provide the outlet from the pre-diffuser 100. The diffusion duct exits 128 (FIG. 6) are larger than the respective diffusion duct inlets 126 which are positioned between each of the EGVs 108. In one example, the number of EGVs are 2-5 times more than the number of diffusion duct inlets 126. In this embodiment, the diffusion passage ducts 124 expand primarily in the radial direction to the diffusion duct exits 128.

The hot fairing structure 102 and the exit guide vane ring 104 include an anti-rotation interface 130 that positions the anti-rotation features 132, 134 in a region of low stress inboard of the diffusion passages 120. In the disclosed embodiment, the hot fairing structure 102 may include a multiple of circumferentially located anti-rotation tabs 132

(FIG. 7) that engage respective anti-rotation slots 134 (FIG. 8) in the exit guide vane ring 104. The inboard location of the anti-rotation features 132, 134 allow the multiple, static, hot components to grow and interact together, with low stress, and simultaneously remain aligned with the rotating components to facilitate a longer service life and engine efficiency.

An axial extension 140 of the hot fairing structure 102 extends along an inner diameter flow surface of the flow passage P. The axial extension 140 at least partially overlaps a recessed area 142 of the exit guide vane ring 104. That is, the axial extension 140 extends in a direction opposite that of the core flow in the flow passage P and overlaps the recessed area 142 (FIG. 8) in the exit guide vane ring 104.

A hot fairing radial flange 150 extends from the hot fairing structure 102 parallel to an exit guide vane radial flange 152 of the exit guide vane ring 104. A static structure flange 154 extends radially outwardly from the static structure 106 with respect to the engine axis A to abut the hot fairing radial flange 150. That is, the static structure flange 154 operates as a mount location for the hot fairing structure 102 and the exit guide vane ring 104. The hot fairing radial flange 150 also includes a multiple of circumferentially located anti-rotation tabs 156 (FIG. 9) opposite the anti-rotation tabs 132 that engage respective anti-rotation slots 158 (FIG. 10) in the static structure flange 154 of the static structure 106.

A clamp ring 160 abuts the exit guide vane radial flange 152 to sandwich a seal member 170 between the exit guide vane radial flange 152 and the hot fairing radial flange 150. A seal member 170, e.g., a torsional spring seal, dogbone, or diamond seal, that accommodates compression of the hot fairing structure 102 and the exit guide vane ring 104 in response to axial assembly of the static structure modules. A multiple of circumferentially arranged fasteners 180 fastens the clamp ring 160 to the static structure 106.

An outer radial interface 190 between the hot fairing structure 102 and the exit guide vane ring 104 includes a radial interface 192 and an axial interface 194. Since the outer radial interface 190 of the hot fairing structure 102 and the exit guide vane ring 104 are devoid of discontinuities and are uniform in cross-section around the circumference of the full hoop structures, service life is significantly increased. The anti-rotation interface 130 and the outer radial interface 190 are essentially hidden from the gas path and are located in low stress regions.

Figure 12:
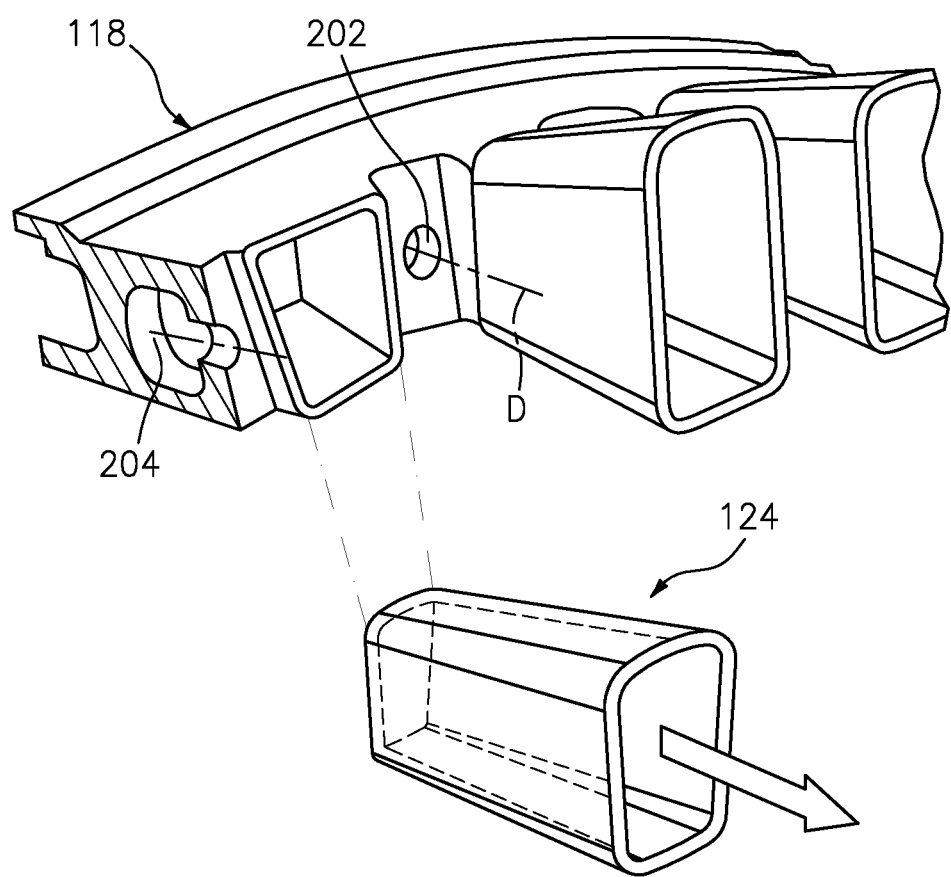
FIG. 12 is an exploded perspective view of the hot fairing structure of the pre-diffuser.

With reference to FIG. 12, the ring-strut-ring structure 118 may be cast from nickel alloys to provide for structural attachment and efficient sealing between turbine engine components combined with independently manufactured thin-wall diffusion passage ducts 124. The diffusion passage ducts 124 can be manufactured by several methods including cast, sheet-metal formed, additively manufactured, or combinations thereof. The wall thickness and local stiffness of the diffusion passage ducts 124 can be tailored to a specific requirement thereof without excessive weight as is typical of cast components. The joining of the diffusion passage ducts 124 to the ring-strut-ring structure 118 to form each complete diffusion passage may be by brazing, bonding, welding, mechanical, or others. Light weight diffusion passage ducts 124 reduce the overall weight of the design, simplify the ring-strut-ring structure 118 casting process, and increase the natural frequencies of the hot fairing structure 102 by minimizing the cantilevered mass of the diffusion passage ducts 124.

Figure 13:
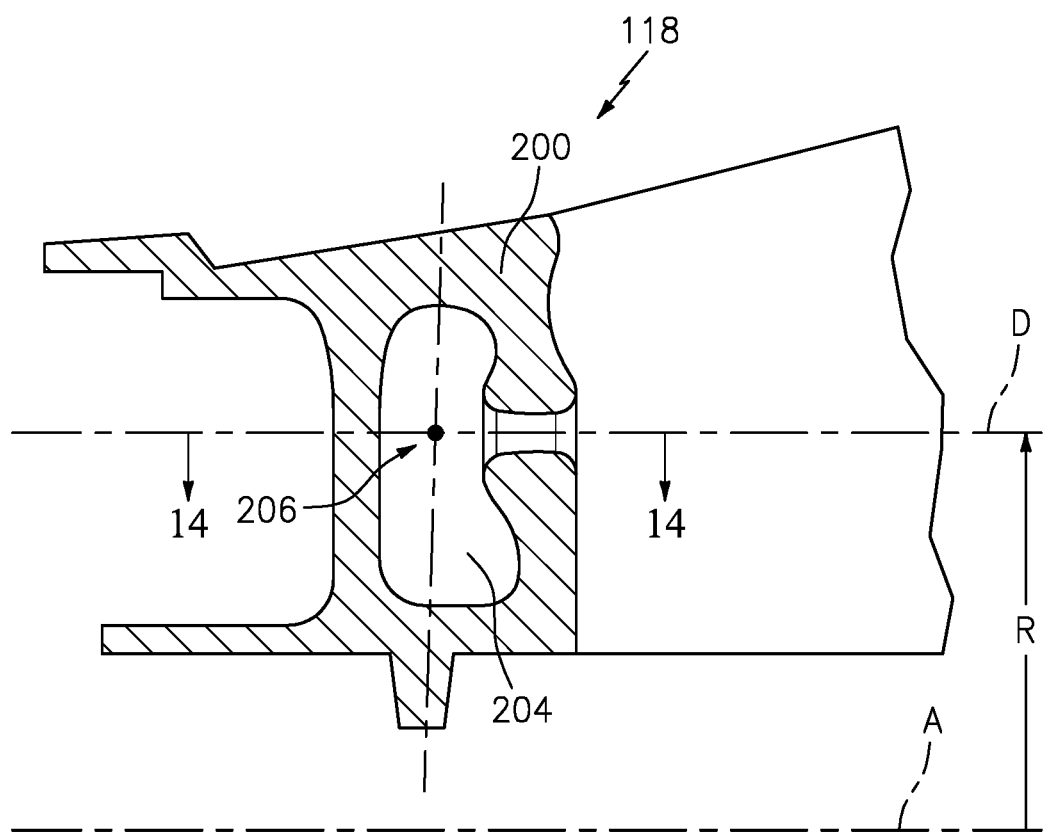
FIG. 13 is an exploded cross-sectional view taken along line 13-13 in FIG. 5.
Figure 14:
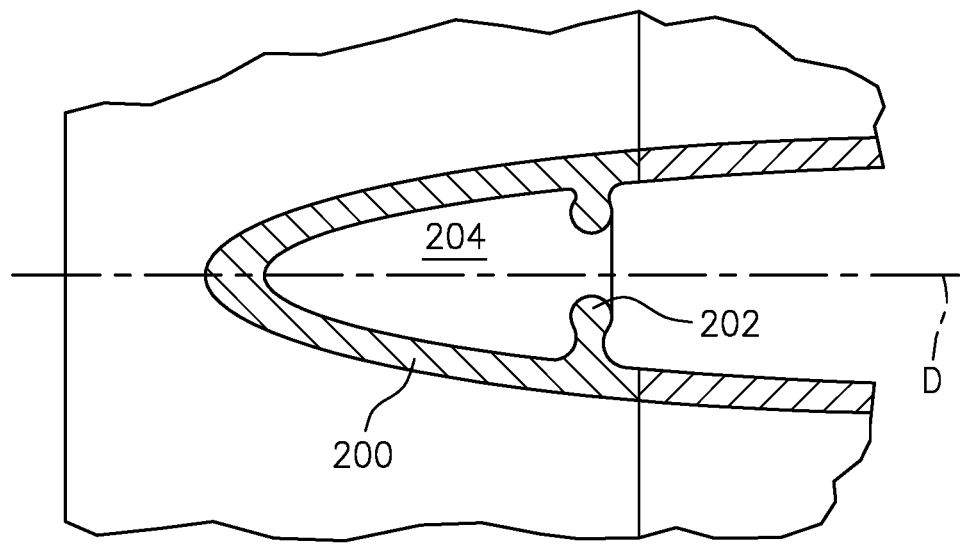
FIG. 14 is an exploded cross-sectional view taken along line 14-14 in FIG. 13.
Figure 15:
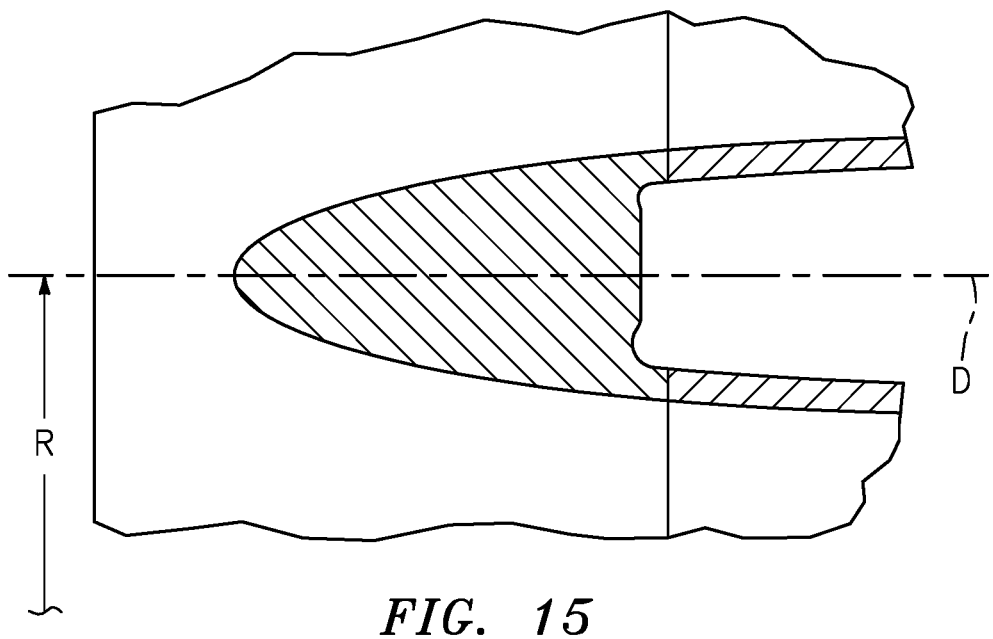
FIG. 15 is an exploded cross-sectional view taken along line 14-14 in FIG. 13 of another embodiment.

With reference to FIG. 13, the one-piece ring-strut-ring structure 118 of the hot fairing structure 102 includes a multiple of hollow struts 200 that align with the respective multiple of upstream EGVs 108 of the exit guide vane ring 104 and split the flow into two adjacent diffusion passage ducts 124 (FIG. 14). Each of the multiple of hollow struts 200 are generally airfoil shaped. In this embodiment, the hollow struts 200 reduce thermal mass and thickness so that the transient thermal gradient within the strut is minimal. The hollow strut 200 includes a cavity 204 that may be manufactured with ceramic cores, and a core exit via a passage 202 may be located at a location that has the least impact on thermal stiffness. Alternatively, the struts 200 may be solid (FIG. 15).

Each passage 202 is located along an axis D and is in communication with the cavity 204 in the hollow strut 200. The passage 202 may be reinforced and permits diffusion air from the diffuser side of the pre-diffuser 100, i.e., the air around the combustor 56, to be received into the respective cavity 204. The diffuser air facilitates thermal control of the ring-strut-ring structure 118 of the hot fairing structure 102 to reduce the mass of the ring-strut-ring structure 118. The reduced mass of the ring-strut-ring structure 118 of the hot fairing structure 102 results in a more responsive thermal characteristic. The strut geometry maximizes the perimeter of the ring-strut-ring structure 118 that is engaged in torsional stiffness. That is, the mass close to the centroid 206 has little to no effect on stiffness. To resist multi-node sinusoidal waves travelling around the circumference of the hot fairing structure 102, local torsional sectional properties of the ring-strut-ring structure 118 facilitate control of the natural frequencies of the hot fairing structure 102.

The ring-strut-ring structure 118 with the hollow regions with the core breakout located close to the centroid 206 of the torsional section forms a pre-diffuser 100 that can have both high natural frequencies and more uniform transient thermal gradients which enables a lightweight, high performance low thermal stress design. The hot fairing structure 102 with a hollow leading edge region and the core opening on the aft side of the hollow strut 200, is located about the mid-axis of the airfoil shape to connect outer diameter static structure, with minimal thermal mass, and an inner diameter static structure with distributed mass such that the transient thermal response is optimized to reduce thermal stress.

The ring-strut-ring structure 118 also allows coupled Exit Guide Vanes with the floating hot fairing to provide improved cyclic life. Light weight tubular flowpath extensions reduce the overall weight of the design, simplify the ring-strut-ring structure 118 casting process, and increase the natural frequencies of the hot fairing by minimizing the cantilevered mass of the tubes. Additionally, the torsionally stiff ring-strut-ring structure 118 ensures that the design can be incorporated with features on the inner diameter structure which facilitates attachment to other structures with the least amount of contact, yet have sufficient frequency margin with respect to engine operating vibration sources.

Although a combination of features is shown in the illustrated examples, not all of them need to be combined to realize the benefits of various embodiments of this disclosure. In other words, a system designed according to an embodiment of this disclosure will not necessarily include all of the features shown in any one of the figures or all of the portions schematically shown in the figures. Moreover, selected features of one example embodiment may be combined with selected features of other example embodiments.

It should be understood that like reference numerals identify corresponding or similar elements throughout the several drawings. It should also be understood that although a particular component arrangement is disclosed in the illustrated embodiment, other arrangements will benefit herefrom.

The foregoing description is exemplary rather than defined by the limitations within. Various non-limiting embodiments are disclosed herein, however, one of ordinary skill in the art would recognize that various modifications and variations in light of the above teachings will fall within the scope of the appended claims. It is therefore to be understood that within the scope of the appended claims, the disclosure may be practiced other than as specifically described. For that reason the appended claims should be studied to determine true scope and content.

What is claimed:

1. A pre-diffuser downstream of a compressor section of a gas turbine engine, comprising:
    a full ring ring-strut-ring structure that comprises a multiple of hollow struts and a multiple of inlets to a multiple of diffusion passages, one of the multiple of inlets and a respective one of the multiple of diffusion passages being between each one of the multiple of hollow struts, wherein each of the multiple of hollow struts comprises a cavity in communication with a combustor section of the gas turbine engine through a passage, wherein the passage has a passage opening on a downstream surface of each of the multiple of hollow struts, and the passage opening is the only inlet or outlet to the cavity for fluidic contact outside of the cavity; and
    a multiple of diffusion passage ducts extending from the ring-strut-ring structure, each of the multiple of diffusion passage ducts in communication with one of the multiple of diffusion passages.

2. The pre-diffuser of claim 1, further comprising:
    an exit guide vane ring adjacent to the ring-strut-ring structure;
    an exit guide vane radial flange that extends transversely from the exit guide vane ring;
    a full ring hot fairing radial flange that extends transversely from the ring-strut-ring structure parallel to the exit guide vane radial flange of the exit guide vane ring;
    a first anti-rotation feature on one side of the full ring hot fairing radial flange and a second anti-rotation feature on an opposite side of the full ring hot fairing radial flange, wherein the first anti-rotation feature engages an exit guide vane ring and the second anti-rotation feature engages a static structure.

3. The pre-diffuser as set forth in claim 2, wherein the first anti-rotation feature and the second anti-rotation feature are not exposed to an engine gas path of the gas turbine engine.

4. The pre-diffuser as recited in claim 1, wherein the inlet to each of the multiple of diffusion passages are smaller than an exit from the diffusion passage.

5. The pre-diffuser as recited in claim 1, wherein each of the multiple of hollow struts align with one of a respective multiple of exit guide vanes of an exit guide vane ring.

6. A pre-diffuser for a gas turbine engine, comprising:
    an exit guide vane ring having a multiple of exit guide vanes defined around an engine longitudinal axis; and
    a hot fairing structure adjacent to the exit guide vane ring to form a multiple of diffusion passages defined around the engine longitudinal axis, the hot fairing structure comprises a ring-strut-ring structure with a multiple of hollow struts and a multiple of inlets to a multiple of diffusion passages, one of the multiple of inlets and a respective one of the multiple of diffusion passages being between each one of the multiple of hollow struts, wherein each of the multiple of hollow struts comprises a cavity in communication with a combustor section of the gas turbine engine through a passage, wherein the passage is closed facing upstream and has a passage opening on a downstream surface of each of the multiple of hollow struts such that air from the combustor section of the gas turbine engine enters the cavity to provide thermal control of the ring-strut-ring structure, wherein the passage opening is the only inlet or outlet to the cavity for fluidic contact outside of the cavity.

7. The pre-diffuser as set forth in claim 6, further comprising:
    a multiple of diffusion passage ducts extending from the ring-strut-ring structure, each of the multiple of diffusion passage ducts in communication with one of the multiple of diffusion passages.

8. The pre-diffuser as recited in claim 6, further comprising:
    an outer radial interface between a radial outer surface of the hot fairing structure and the exit guide vane ring, the outer radial interface being a full hoop structure; and
    an anti-rotation feature between the hot fairing structure and the exit guide vane ring, the anti-rotation features inboard of the multiple of diffusion passages.

9. The pre-diffuser as recited in claim 8, wherein the outer radial interface and the anti-rotation feature are not exposed to an engine gas path of the gas turbine engine.

10. The pre-diffuser as recited in claim 6, further comprising:
    a hot fairing radial flange that extends radially inward from the hot fairing structure; and
    an exit guide vane radial flange that extends radially inward from the exit guide vane ring, the seal located between the exit guide vane radial flange and the hot fairing radial flange.

11. The pre-diffuser as recited in claim 6, further comprising:
    a static structure flange that abuts the hot fairing radial flange;
    a clamp ring that abuts the exit guide vane radial flange; and
    a multiple of fasteners that fasten the clamp ring to the static structure flange.

* * * * *